United States Patent [19]
Dittrich et al.

[11] Patent Number: 6,129,392
[45] Date of Patent: Oct. 10, 2000

[54] COUPLER FOR TUBULAR-SHAFT INSTRUMENTS

[75] Inventors: Horst Dittrich, Immendingen; Uwe Bacher; Michael Sauer, both of Tuttlingen, all of Germany

[73] Assignee: Karl Storz GmbH & Co. KG, Germany

[21] Appl. No.: 08/945,006

[22] PCT Filed: Apr. 15, 1996

[86] PCT No.: PCT/DE96/00650

§ 371 Date: Dec. 26, 1997

§ 102(e) Date: Dec. 26, 1997

[87] PCT Pub. No.: WO96/32068

PCT Pub. Date: Oct. 17, 1996

[30] Foreign Application Priority Data

Apr. 13, 1995 [DE] Germany ............................ 195 14 098

[51] Int. Cl.[7] .................................................. F16L 37/18
[52] U.S. Cl. ............................................ 285/314; 285/316
[58] Field of Search .................................. 285/316, 277, 285/314, 315

[56] References Cited

U.S. PATENT DOCUMENTS

| | | |
|---|---|---|
| 1,868,587 | 7/1932 | Richards .................................. 285/314 |
| 3,032,359 | 5/1962 | Cator ....................................... 285/277 |
| 3,083,042 | 3/1963 | Collar ...................................... 284/314 |
| 3,351,359 | 11/1967 | Ferrairs ................................... 285/314 |
| 4,403,959 | 9/1983 | Hatakeyama . |
| 4,444,223 | 4/1984 | Maldavs .................................. 285/277 |
| 4,577,875 | 3/1986 | Miyakawa . |

FOREIGN PATENT DOCUMENTS

| | | |
|---|---|---|
| 2465467 | 4/1981 | France . |
| 43 11 161 | 10/1994 | Germany . |

*Primary Examiner*—Eric K. Nicholson
*Attorney, Agent, or Firm*—St. Onge Steward Johnston & Reens LLC

[57] ABSTRACT

A coupling assembly for connecting a handle to an instrument extending along a longitudinal axis has a coupler, which releasably receives the handle and has an outer sleeve and a snap-in sleeve formed with a snap-in element. The handle has a recess receiving the snap-in element which is guided along a conical recess formed in the outer sleeve to move to a locking position wherein the handle and the coupler are displaceably fixed relative each other. The outer sleeve is rotatable about the longitudinal axis and its recess has a periphery formed with an inner surface enabling the snap-in element to move radially from the locking position during rotation so as the handle can be axially withdrawn from the coupler.

17 Claims, 5 Drawing Sheets

Schnitt ohne 2,3 gezeichnet

COUPLER FOR TUBULAR-SHAFT INSTRUMENTS

DESCRIPTION

1. Field of the Invention

The invention relates to coupler for tubular-shaft instruments, which serves to fasten an instrument or part of an instrument such as an (instrument) handle detachably on a shaft tube.

2. Prior Art

In endoscopic application and particularly in microsurgery it is often necessary to insert an endoscope, a trocar, forceps, scissors or another instrument into a shaft which may be a universal shaft, a trocar sleeve or the like, for instance. It is necessary in many applications that the instrument inserted into the shaft be securely connected to the shaft in operation and may be detached again whenever this is necessary. Normally a coupler is provided to establish this secure connection. These couplers are manufactured in the most different versions by the individual producers. As a rule, these couplers include bayonet mount elements and a rotating ring which must be rotated in the opposite direction for locking and unlocking.

Independently thereof, there is an ever-increasing demand for instruments and particularly tubular-shaft instruments or endoscopes which may be dismantled with a few manipulations for cleaning and sterilizing the instruments before and/or after a surgical operation, without residues remaining adhered in corners of the instruments which are difficult to reach, e.g. angled corners. In such a case, too, the use of couplers is required which ensure the easy disassembly of instruments and tubular-shaft instruments in particular.

Moreover, it is frequently desirable to use at least those instrument parts only once which come into contact with the patient's body. In order to be able to offer the frequently highly complex instruments yet at the most reasonable price possible it makes sense to design those parts which do not contact the patient's body as non-disposable elements. In such a case, too, it is necessary to provide couplers or the like in order to enable a rapid, simple and reliable exchange of instrument parts.

The German Patent DE 39 34 610 A1 discloses a quick-action coupler for surgical instruments. That quick-action coupler includes a plug-in pin with at least one shoulder in its peripheral surface. A casing of the quick-action coupler is provided with a plug-in opening for the plug-in pin. At least one locking body designed for radial and axial displacement is provided in the wall of the casing, which, when the plug-in pin is inserted, is aligned relative to the shoulder. A sliding piece supported on the casing for displacement between two terminal positions bears against the locking body in a first terminal position, sliding the latter inwardly beyond the inner wall of the plug-in opening into the latter. In the second terminal positions, the sliding piece releases the path for the locking body so that the latter may be radially outwardly displaced until it is no longer inserted into the plug-in opening. However, it is not known from that prior art document that a rotating sleeve disposed around a shaft mount should be provided in a quick-action coupler, which is used to disengage the connection simply by rotation rather than by a sliding movement.

The European Patent EP 0 056 266 A1 discloses a quick-exchange chuck which is suitable for use between driving parts and/or tools having driving jaws for rotational drive and key-way engagement for detachable longitudinal connection, particularly for surgical instruments. There a locking sleeve, which serves as driving element, is provided with a radially displaceable locking element, which sleeve is surrounded by a push-on locking ring which, due to a locking cam, causes locking with the introduced driving element or tool when the locking element is rotated, with an annular spring engaging into the locking ring, on the one hand, which spring engages, on the other hand, into a closing ring which is adapted to be inserted by means of a locking pin at an opening on the locking sleeve, possibly with an annular insert, up to an annular groove and may be locked under spring action relative to the opening.

This prior art quick-exchange chuck presents, however, a comparatively complex structure and does not permit a rapid, simple and reliable exchange of the parts of the instrument by the user. Moreover, sterilization of this quick-exchange chuck ought to be difficult.

Apart from the aforementioned disadvantages, all the aforementioned couplers display the disadvantage that the operator is required to perform an intentional external manipulation for both locking and unlocking the coupler.

DESCRIPTION OF THE INVENTION

The present invention is now based on the problem of defining a coupler for tubular-shaft instruments which permits a rapid and simple detachable secure interconnection between parts of tubular-shaft instruments, permitting a reliable handling after connection of these parts. In particular, the inventive coupler is intended to allow for a connection of the parts to be coupled to each other, without an intentional manipulation being required on the coupler.

One inventive solution to this problem is defined in the independent patent claims. Improvements of the present invention are disclosed in the dependent claims.

The present invention starts out from a coupler for tubular-shaft instruments, which connects detachably an instrument or a part of an instruments such as a handle to a shaft tube and includes a rotating sleeve disposed around a shaft mount. Moreover, a locking sleeve such as a spherical sleeve is provided which is disposed between the rotating sleeve and the shaft mount and which is adapted for movement in an axial direction defined by the longitudinal axis of the shaft tube and for receiving at least one snap-in element such as a ball which is adapted for moving radially outwards, i.e. away from the longitudinal axis of the shaft tube. The handle, which presents at least one recess on its outer surface at its end reaching the coupler, is connected by insertion of this handle end into the coupler by snapping the ball or balls, respectively, into the recess or recesses.

This provision permits a rapid and simple connection of the shaft tube. The inventive coupler presents the particular advantage that it is not necessary to manipulate the rotating sleeve for locking the coupler. The coupling action is rather automatic. The rotating sleeve must only be rotated for unlocking the coupler.

Due to the conical design of the recess on the handle it is now possible that the snap-in element, such as the ball or balls received by the spherical sleeve, may be engaged in the recess so that a secure connection is achieved in correspondence with the magnitude of the frictional forces and resetting forces.

When the handle is inserted the snap-in element or snap-in elements is/are forcibly moved by one end of the handle along an inclination. As a result, the ball is urged out of the region into which the end of the handle is inserted and is subsequently caused to snap back under the action of appropriate resetting forces. The inclination, which may be disposed in the rotating sleeve, is expediently conical.

It is moreover highly expedient to have an angle, which is defined by the axis and the inclination, which is wider than the angle defined by the axis and the recess. With this provision the space for the balls is narrowed in an axial direction when the balls snap into the recesses. With a resetting force it is achieved that the balls are pressed into the narrowing gap, get jammed and fixedly center the coupler on the instrument. It is sensible in this design that the resetting force urges the spherical sleeve and hence the balls in a direction towards their initial position.

The resetting force is expediently achieved by a spring such as a helical or compression spring producing a defined force. With an appropriate device it is possible to vary this force by varying the spring constant. In this way it is possible, for instance, to use pneumatic springs as compression springs, producing an adjustable pneumatic pressure.

In accordance with the present invention, the coupler is connected to the handle or/and the coupler is connected to the shaft tube as follows:

the handle is inserted into the shaft mount and contacts at least one snap-in element, when the handle is further inserted the snap-in element is displaced up to a position most remote from the initial position, and by a continuing movement of the handle the snap-in element is moved back into the recess on the handle.

There, the balls are jammed and the coupler is centers on the instrument or the shaft tube, respectively.

The removal of the shaft tube or the handle, respectively, from the coupler becomes possible by simultaneous rotation of a rotating sleeve and drawing out the instrument. To this end it is expedient to provide a recess disposed in the rotating sleeve, which is limited partly by the aforementioned inclination, with cross-sectional areas of different sizes along the circumference of the rotating sleeve. On account of a rotation of the rotating sleeve relative to the spherical sleeve in a way that the recess above the ball or the balls, respectively, has a wider cross-sectional area these balls are enabled to evade the pressure due to the traction on the handle and hence to evade the transmitted force produced by the respective recess on the appertaining ball in a vertical direction from the longitudinal axis. With this provision the handle is rendered detachable.

It is furthermore expedient to cause a resetting force to urge the rotating sleeve in a direction towards its initial position. This resetting force may be achieved, for instance, by a spiral spring. If the option is desirable that the resetting force is adjustable a pneumatic spring is apparent as spring means in this case, too, so as to allow for adjustability of the pneumatic pressure.

It is also possible to provide for a releasable secure engagement of a pin in a hole or a groove so as to prevent the rotating sleeve from rotation when the handle or the shaft tube is snapped into the coupler, instead of or in addition to a resetting force produced by a spring.

The coupler is expediently used for tubular-shaft instruments.

Another solution to the problem is achieved by a coupler including the following features:
a spherical sleeve receiving at least one ball, which ball or balls is/are adapted for outward movement,
a rotating sleeve having a recess around its circumference, which is limited at least by an inclination and projects into the rotating sleeve over different lengths, wherein the spherical sleeve is adapted for displacement in a horizontal direction and is contacted with the rotating sleeve at least in part, and wherein
the ball or the balls is/are carried along with the spherical sleeve both horizontally and additionally in a vertical direction, with the deflection of the respective ball being limited by the inclination and the vertical extension of the recess.

In order to permit a detachable secure connection of this coupler to a handle or/and a shaft tube at least one recess is provided on the end of the handle or the shaft tube, respectively, into which the ball, or in case of several recesses the balls, engage(s) upon mounting.

The connection is maintained by resetting forces of at least one spring and/or by positively locking pins.

BRIEF DESCRIPTION OF THE DRAWING

The following is an exemplary description of the invention without any limitation of the general inventive idea, with reference to embodiments and on the basis of the drawings to which explicit reference is made in all other respects in relation to the disclosure of all inventive details which are not explained exhaustively in the text. In the drawing.

DESCRIPTION OF EMBODIMENTS

Figure 1:
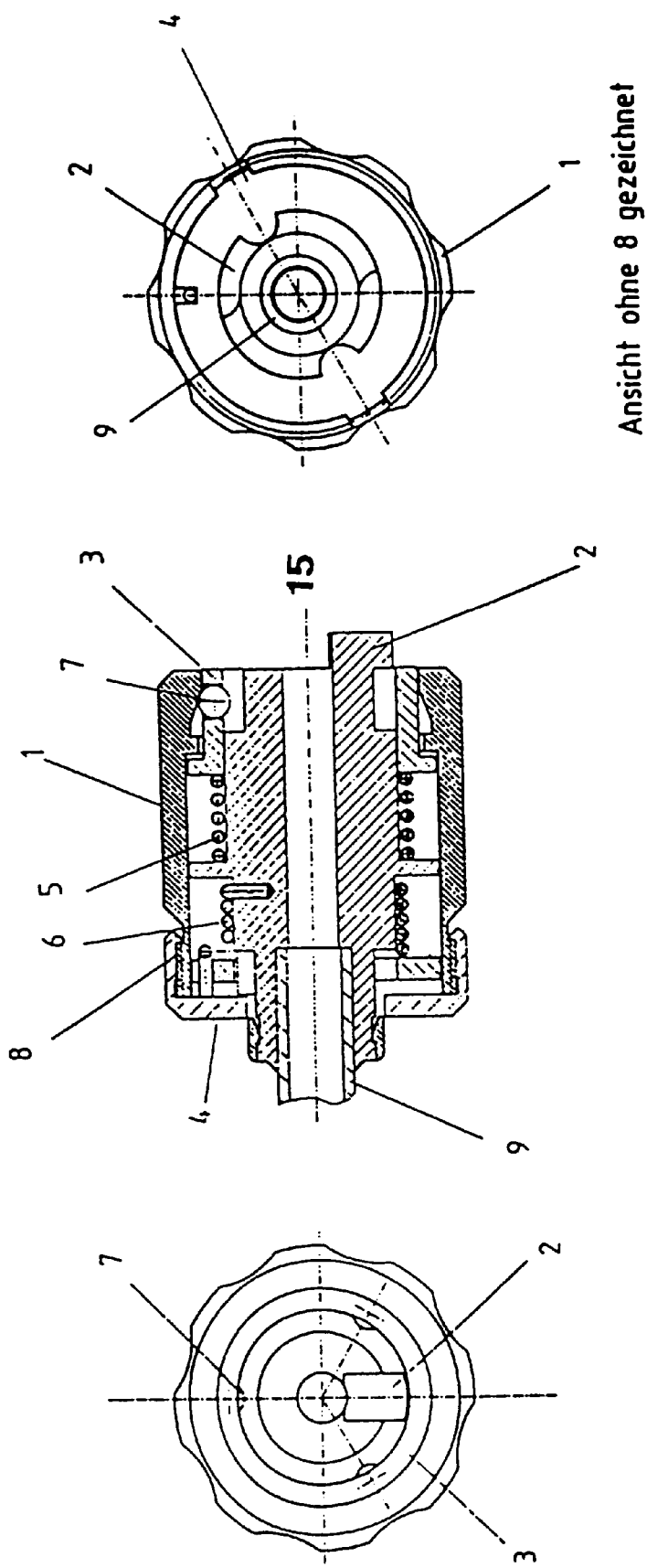
FIG. 1: shows a cross-sectional view taken through an inventive coupler in the middle, with part of a shaft tube being shown on the left side, and with a view of the middle figure from the left side being shown on the left side and with a view of the middle figure from the left side being illustrated on the right side of the illustration, without showing the covering sleeve.

Equal or corresponding elements are indicated by the same reference numerals throughout the following figures so that a repeated discussion will be omitted and merely the variations of the embodiments illustrated in these figures versus the first embodiment will be explained:

FIG. 1 shows an initial position of an inventive coupler which serves the function of establishing and separating the connection between the shaft tube and the instrument handle 10 as an example of an instrument or part of an instrument in the case of tubular-shaft instruments suitable for disassembly, with the coupler of this embodiment being securely connected to the shaft tube 9.

It is, of course, also possible, however, to dispose the coupler also on the instrument part 10 rather than on the shaft tube 9.

Figure 4:
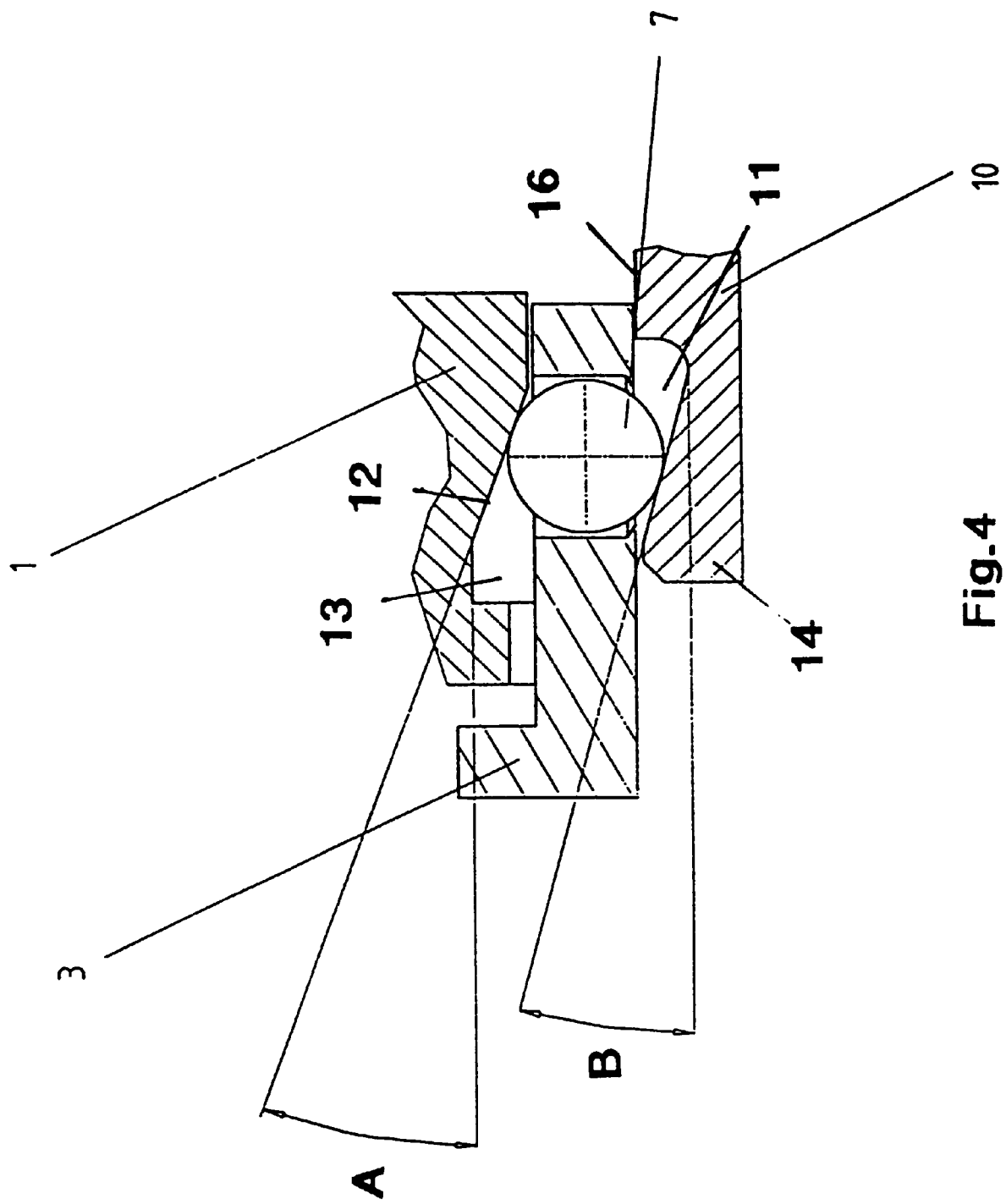
FIG. 4: a detail from FIG. 3, and FIG. 5: a view in correspondence with FIG. 3 during unlocking of the coupler with the handle.

What is illustrated is a rotating sleeve 1 having a recess 13 along its inner periphery. This recess is shown in an enlarged view in FIG. 4.

A ball 7, which is disposed in the axially movable sleeve 3, projects into the recess 13.

The axially movable sleeve is urged into its initial position by a compression spring. The resetting force of a spring 6 subject to torsion prevents the rotating sleeve 1 from unintentional rotation.

The coupler is protected from penetration of foreign matter such as dirt on the shaft tube side by a contact disk 4 and a covering sleeve.

Figure 2:
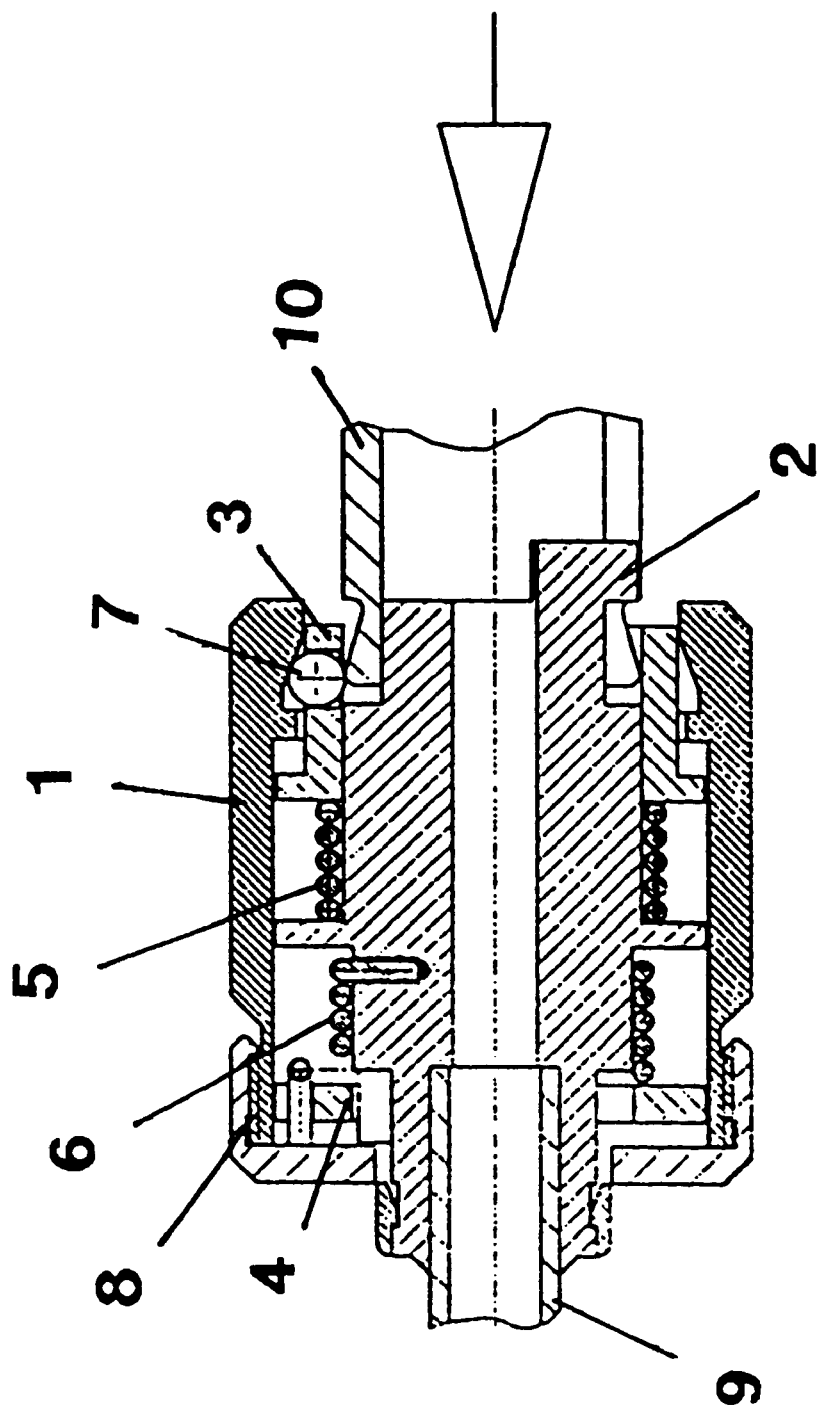
FIG. 2: a cross-sectional view of the coupler shown in FIG. 1, with one part of a handle.

The coupler is axially pushed onto the handle 10 for connecting the coupler with the handle 10. In this movement, the rear side of the shaft mount 2 is concentrically guided into the bore of the handle 10. When the handle is introduced the front edge of the handle 14 produces a pressure on the balls 7 in the axially movable sleeve 3 (cf. FIG. 2). The balls bear against the conical inclination of the rotating sleeves 1.

On account of the spring force of the compression spring 5 being overcome, the sleeve 3 is pushed back together with the balls 7, and the balls 7 slide outwardly along the conical inclination on the rotating sleeve 1. The deflection of the balls corresponds to the increase of diameter of the conical surface or inclination 12 in the recess 13.

In this manner, the lumen or cross-sectional area into which the terminal region 14 of the handle is inserted, is increased, particularly to a size that the terminal region of the handle may be inserted by a longer distance than this were possible by virtue of the initial position of the balls.

The resetting force of the compression spring 5 causes the sleeve 3 to return into the initial position over the outer diameter or the outer surface 16 of the handle 10. With this provision the balls 7 are urged inwards again by the conical inclination 12 in the rotating sleeve 1 and are located in the conical recess(es) 11 in the handle 10.

Figure 3:
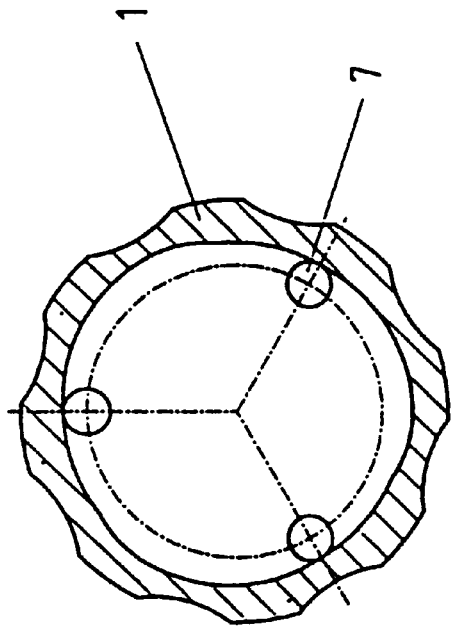
FIG. 3: left: like FIG. 2 with the handle engaged; right: sectional view as indicated on the left side, without illustration of the shaft mount and the spherical sleeve.
Figure 3:
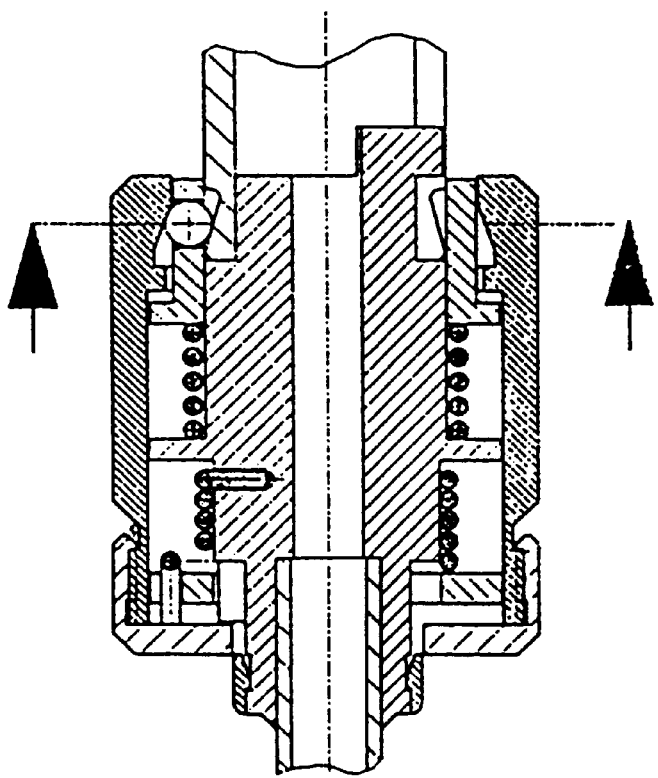

Now the handle is snapped into the coupler (cf. FIG. 3). What is expedient in this configuration—as may be roughly seen in FIG. 4—is the fact that the angle A of the conical inclination in the rotating sleeve is wider than the angle B in the recess on the handle. The space for accommodation of the balls 7 is handle reduced upon snap-in or locking engagement in an axial direction. Under the force of the compression spring 5 it is achieved that the balls 7 are pressed into the narrowing gap, get jammed there, and that the coupler is securely centered on the handle.

Figure 5:
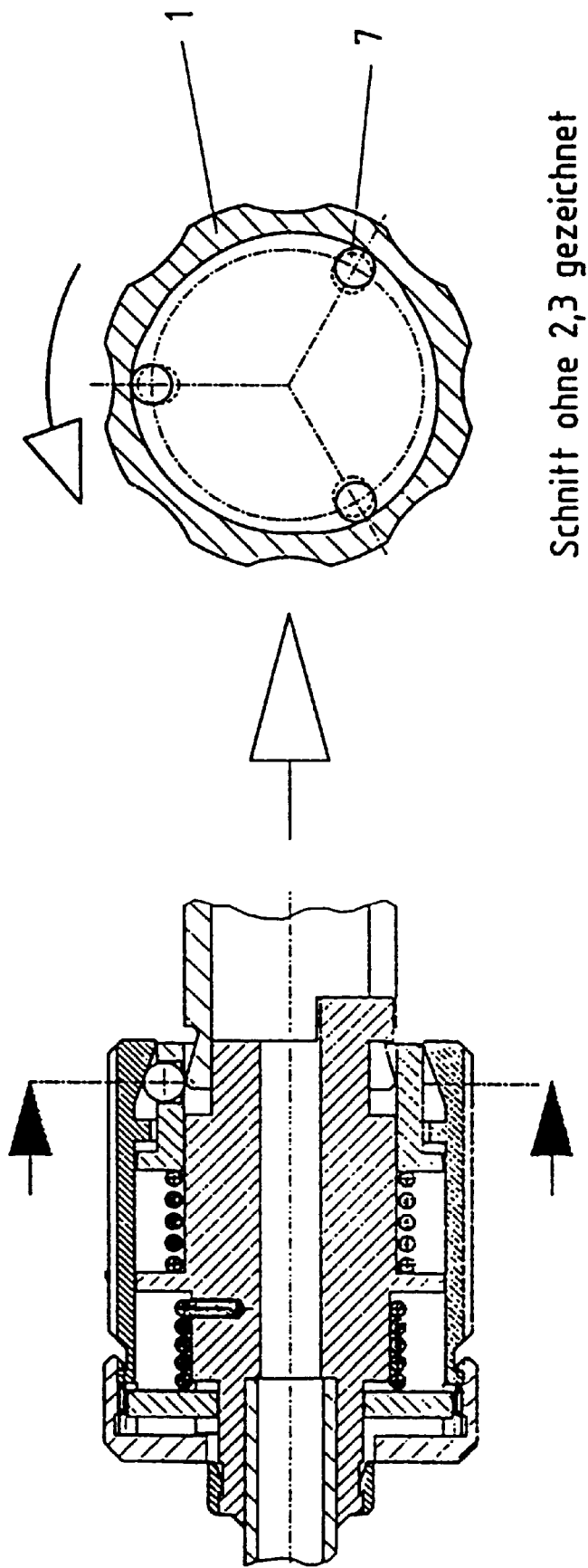

For detachment of the coupler from the handle 10, in accordance with FIG. 5, the rotating sleeve 1 is rotated in opposition to the bias produced by the spring 6 subject to torsion, e.g. in a direction to the left when seen from the tubular-shaft side, and then the handle 10 is withdrawn. As the rotating sleeve 1 is rotated the recess of the eccentrically conical inclinations, which are positioned above the balls, is widened. As a result, the balls 7 an move away from the groove or recess in the handle 10 in an outward direction, so as to release same, which movement is triggered by the traction on the handle 10. The handle 10 is now detached again from the coupler. As soon as the rotating sleeve 1 is released this sleeve rotates back into the initial position under the resetting force produced by the spring 6 subject to torsion. detached again from the coupler. After the rotating sleeve 1 has been is connecting and detaching The connection is maintained by resetting forces of at least one spring and/or by positively locking pins.

What is claimed is:

1. A coupling assembly comprising:
    a shaft tube having a longitudinal axis;
    a tubular-shaft instrument spaced axially apart from said shaft tube; and
    a coupler releasably connecting said shaft tube and said tubular-shaft instrument and comprising: a rotating sleeve disposed around a shaft mount, wherein said tubular-shaft instrument on its end includes at least one recess, and wherein a snap-in sleeve is disposed between said rotating sleeve and said shaft mount, which is adapted for movement in an axial direction defined by the longitudinal axis of said shaft tube and which receives at least one snap-in element adapted for movement to the outside, and wherein the connection of said tubular-shaft instrument to said coupler is established by snap engagement of said at least one snap-in element in said at least one recess, said rotating sleeve being rotationally arrested upon detachable engagement of a pin into a hole after said coupler has received the tubular shaft instrument.

2. The coupling assembly according to claim 1, wherein said at least one recess has a conical configuration.

3. The coupling assembly according to claim 1, wherein said movable snap-in sleeve is a sleeve and wherein said snap-in elements are balls.

4. The coupling assembly according to claim 1, wherein when said instrument is inserted said snap-in element is forcibly moved through one end of a handle along an inclination.

5. The coupling assembly according to claim 4, wherein said inclination has a conical configuration.

6. The coupling assembly according to claim 4, wherein angle (A) defined by said axis and said inclination is wider than angle (B) formed by said axis and said recess.

7. A coupling assembly comprising:
    a tubular-shaft instrument having a handle;
    a shaft tube spaced from said handle;
    a shaft mount between said tubular-shaft handle;
    a rotating sleeve disposed around said shaft mount, wherein
    said handle, on its end includes at least one recess, and wherein a snap-in sleeve is disposed between said rotating sleeve and said shaft mount and is biased under a resetting force produced by a spiral spring, in a direction towards an initial position, said snap-in sleeve being adapted for movement in an axial direction defined by a longitudinal axis of said shaft tube and receiving at least one snap-in element adapted for movement to the outside, and wherein the connection of said instrument to said coupler is established by snap engagement of said at least one snap-in element in said at least one recess.

8. The coupling assembly according to claim 4 including characterized in that a recess (13) in said rotating sleeve which is limited partly by said inclination (12), and presents cross-sectional areas of different sizes along a periphery of said rotating sleeve.

9. The coupling assembly according to claim 7, wherein when said rotating sleeve (1) is rotated out of its initial position said at least one snap-in element (7) may project into said recess (13) over a longer distance so as to be releasable from said recess (11) on said handle.

10. The coupling assembly according to claim 1, wherein said instrument is an endoscopic instrument.

11. The coupling assembly according to claim 1, including an endoscopic instrument received in said shaft tube.

12. A method of connecting at least part of an instrument to a shaft tube, with use of a coupler comprising the steps of:
    pushing part of an instrument into a shaft mount and contacting a snap-in element received in a snap-in sleeve,
    slidably moving the instrument part to displace the snap-in element up to a position remotest from an initial position,
    resiliently biasing a snap-in sleeve receiving the snap-in element in a direction opposite to a direction of the pushing of the instrument, thereby moving the snap-in element back towards the initial position and into a recess on the instrument part to lock the shaft tube and the instrument part, and uncoupling the instrument part by rotating an outer sleeve surrounding the snap-in element and axially pulling said sleeve and said instrument part apart.

13. A coupler including:

a snap-in sleeve receiving at least one ball, said at least one ball adapted for moving outwardly, a rotating sleeve including a recess along its circumference, which recess is limited by an inclination at least partly and projects into said rotating sleeve over different lengths, wherein said snap-in sleeve is adapted for being displaced in a horizontal direction and contacts, at least partly, said rotating sleeve (1), and wherein said at least one ball is moved in a horizontal direction along with said snap-in sleeve and is additionally adapted for vertical movement, with the deflection of said ball being limited by the inclination and the vertical extension of said recess; and a shaft tube received in said coupler by resetting forces of at least two springs and having at least one recess for engagement of said at least one ball.

14. The coupler of claim 13, including a shaft tube (9) received therein, said shaft tube having at least one recess (11) for engagement of said at least one ball (7).

15. The coupler of claim 13, wherein said shaft tube is received by positively locking pins.

16. A coupling assembly comprising:

a shaft having a longitudinal axis;

an instrument holder spaced axially from the shaft, one of said shaft and instrument holder having a first recess; and a coupler for releasably connecting said shaft and said instrument holder and comprising:

a snap-in sleeve axially displaceable between said shaft and said instrument holder, a snap-in element connected to said snap-in sleeve and axially moveable therewith in said first recess to a locking position thereof, wherein said shaft and said instrument holder are displaceably fixed relative each other, and an outer sleeve having an inner periphery formed with cross-sectional areas of different sizes and surrounding said snap-in sleeve, said snap-in element being radially displaceable from its locking position toward said periphery of said second recess upon rotation of said outer sleeve about said longitudinal axis to enable said instrument holder to be disengaged from said shaft.

17. A coupler assembly comprising:

an outer sleeve extending along a longitudinal axis and formed with a first recess, said first recess having a conical surface;

an inner sleeve releasably connectable to outer sleeve, said inner sleeve having a second recess with a conical surface facing said surface of the first recess and forming a space therewith upon relative axial displacement of said sleeves, one of said surfaces being formed eccentrically with respect to said longitudinal axis; and a snap-in element received in said space and movable axially along said conical surfaces to a locking position, wherein said outer and inner sleeves are displaceably fixed relative each other, said snap-in element being displaceable radially during rotation of said outer and inner sleeves relative each other upon applying an external force thereto in the locking position to enable disengagement of said outer and inner sleeves.

* * * * *